United States Patent
Shimmura et al.

(10) Patent No.: US 10,501,725 B2
(45) Date of Patent: *Dec. 10, 2019

(54) METHOD FOR PRODUCING THERAPEUTIC CORNEAL ENDOTHELIAL SUBSTITUTE CELL SPHERE

(71) Applicant: KEIO UNIVERSITY, Tokyo (JP)

(72) Inventors: Shigeto Shimmura, Tokyo (JP); Shin Hatou, Tokyo (JP); Kazuo Tsubota, Tokyo (JP)

(73) Assignee: KEIO UNIVERSITY, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/535,032

(22) PCT Filed: Dec. 11, 2015

(86) PCT No.: PCT/JP2015/084857
§ 371 (c)(1),
(2) Date: Jun. 9, 2017

(87) PCT Pub. No.: WO2016/093359
PCT Pub. Date: Jun. 16, 2016

(65) Prior Publication Data
US 2017/0340677 A1 Nov. 30, 2017

(30) Foreign Application Priority Data
Dec. 11, 2014 (JP) ................. 2014-251236

(51) Int. Cl.
| | | |
|---|---|---|
| C12N 5/00 | (2006.01) | |
| C12N 5/079 | (2010.01) | |
| A61K 38/22 | (2006.01) | |
| A61K 38/28 | (2006.01) | |
| A61K 47/36 | (2006.01) | |
| A61K 31/203 | (2006.01) | |
| A61K 35/44 | (2015.01) | |
| C12N 5/10 | (2006.01) | |
| A61K 35/30 | (2015.01) | |
| A61K 48/00 | (2006.01) | |
| A61P 27/02 | (2006.01) | |
| A61F 9/00 | (2006.01) | |

(52) U.S. Cl.
CPC .......... *C12N 5/0621* (2013.01); *A61K 31/203* (2013.01); *A61K 35/30* (2013.01); *A61K 35/44* (2013.01); *A61K 38/22* (2013.01); *A61K 38/28* (2013.01); *A61K 47/36* (2013.01); *A61K 48/0091* (2013.01); *A61P 27/02* (2018.01); *C12N 5/10* (2013.01); *A61F 9/0017* (2013.01)

(58) Field of Classification Search
CPC ...... C12N 5/0621; A61K 35/30; A61F 9/0017
See application file for complete search history.

(56) References Cited

U.S. PATENT DOCUMENTS

| | | |
|---|---|---|
| 5,604,244 A | 2/1997 | DeSantis, Jr. et al. |
| 5,811,453 A | 9/1998 | Yanni et al. |
| 7,959,939 B2 | 6/2011 | Yamagami et al. |
| 9,347,042 B2 | 5/2016 | Shimmura et al. |
| 9,376,661 B2 | 6/2016 | Shima et al. |
| 9,890,357 B2* | 2/2018 | Osafune ............... C12N 5/0605 |
| 2005/0214259 A1 | 9/2005 | Sano et al. |
| 2007/0238173 A1 | 10/2007 | Yamagami et al. |
| 2009/0232772 A1 | 9/2009 | Amano et al. |
| 2012/0142005 A1* | 6/2012 | Hosoya ............... G01N 33/5023 435/6.12 |
| 2012/0207744 A1 | 8/2012 | Mendlein et al. |
| 2013/0023050 A1 | 1/2013 | Shima et al. |
| 2013/0217005 A1* | 8/2013 | Snoeck ................. C12N 5/0617 435/6.1 |
| 2014/0127803 A1 | 5/2014 | Hayashi et al. |
| 2014/0170751 A1 | 6/2014 | Hayashi et al. |

(Continued)

FOREIGN PATENT DOCUMENTS

| | | |
|---|---|---|
| EP | 2532738 A1 | 12/2012 |
| JP | 2001-503423 A | 3/2001 |

(Continued)

OTHER PUBLICATIONS

Wu and Hochedlinger. Nature Cell Biology 13(11):497-505, 2011 (Year: 2011).*
Viscoat Product Sheet. Printed from http://home.intekom.com/pharm/alcon/viscoat.html, pp. 1-3, printed Jun. 8, 2018 (Year: 2018).*
Lee et al. Nature Protocol 2010,vol. 5, No. 4, 688-701 (Year: 2010).*
Koizumi et al., "Development of new therapeutic modalities for corneal endothelial disease using somatic stem cells," *Journal of Clinical and Experimental Medicine*, 241(10): 765-770 (2012).
Poyer et al., "New method to measure the retention of viscoelastic agents on a rabbit corneal endothelial cell line after irrigation and aspiration," *J. Cataract Refract. Surg.*, 24(1): 84-90 (1998).

(Continued)

*Primary Examiner* — Marcia S Noble
(74) *Attorney, Agent, or Firm* — Leydig, Voit & Mayer, Ltd.

(57) ABSTRACT

The problem of the present invention is to provide a method of efficiently producing therapeutic alternative corneal endothelial cells, particularly, a method capable of stably producing them in a condition suitable for intraocular transplantation (in the anterior chamber) in a large amount. Furthermore, the present invention aims to provide a composition for transplantation, which is preferable for intraocular administration, particularly, into the anterior chamber. A therapeutic alternative corneal endothelial cell sphere can be produced by culturing stem cells in suspension in a differentiation induction medium containing a GSK3 inhibitor, retinoic acid and a ROCK inhibitor. Addition of a viscoelastic substance during intraocular (into the anterior chamber) transplantation of the sphere or cultured corneal endothelial cells dispersed into single cells can increase the number of adherent cells after transplantation.

11 Claims, 5 Drawing Sheets

(56) References Cited

U.S. PATENT DOCUMENTS

| | | | |
|---|---|---|---|
| 2014/0315305 A1 | 10/2014 | Shimmura et al. | |
| 2015/0374881 A1 | 12/2015 | Yamagami et al. | |
| 2017/0253855 A1* | 9/2017 | Nishida | C12N 5/0621 |

FOREIGN PATENT DOCUMENTS

| | | |
|---|---|---|
| JP | 2001-506651 A | 5/2001 |
| JP | 2004-024852 A | 1/2004 |
| JP | 2005-229869 A | 9/2005 |
| JP | 2006-187281 A | 7/2006 |
| JP | 2009-268433 A | 11/2009 |
| WO | WO 2011/096593 A1 | 8/2011 |
| WO | WO 2013/051722 A1 | 4/2013 |
| WO | WO 2014/104366 A1 | 7/2014 |

OTHER PUBLICATIONS

Yamagami et al., "Regenerative engineering of anterior portion of the eye (4) Regenerative Engineering of the corneal endothelium," *Japanese Journal of Clinical Ophthalmology*, 59(11): 182-186 (2005).

Japanese Patent Office, International Preliminary Report on Patentability in International Patent Application No. PCT/JP2015/084857 (dated Nov. 21, 2016).

Japanese Patent Office, International Search Report in International Patent Application No. PCT/JP2015/084857 (dated Mar. 8, 2016).

Aggarwal et al., "Deep lamellar keratoplasty—an alternative to penetrating keratoplasty," *Br. J. Ophthalmol.*, 81(3): 178-179 (1997).

Hato et al., "Induction of differentiation of corneal stroma stem cell into corneal endothelial cell," *Japan Cornea Society Sokai—Keratoplasty Society of Japan Program Shorokushu*, 35(27): 59, Abstract No. 68 (2011).

Hato et al., "Induction of differentiation of corneal stroma stem cell into corneal endothelial cell," *Regenerative Medicine*, 10(supplemental): 163, Abstract No. O-17-1 (2011).

Hatou et al., "Functional Corneal Endothelium Derived from Corneal Stroma Stem Cells of Neural Crest Origin by Retinoic Acid and Wnt/β-Catenin Signaling," *Stem Cells and Development*, 22(5): 828-839 (2013).

Ittner et al., "Compound developmental eye disorders following inactivation of TGFβ signaling in neural-crest stem cells," *J. Biol.*, 4(3): 11 (2005).

Ju et al., "Derivation of Corneal Endothelial Cell-Like Cells from Rat Neural Crest Cells In Vitro," *PLoS One*, 7(7): e42378 (2012).

Kumar et al., "Retinoic acid signaling in perioptic mesenchyme represses Wnt signaling via induction of Pitx2 and Dkk2," *Developmental Biology*, 340(1): 67-74 (2010).

Okumura et al., "Enhancement on Primate Corneal Endothelial Cell Survival In Vitro by a ROCK Inhibitor," *Investigative Ophthalmology & Visual Science*, 50(8): 3680-3687 (2009).

Price et al., "Descemet's Stripping With Endothelial Keratoplasty in 50 Eyes: A Refractive Neutral Corneal Transplant," *Journal of Refractive Surgery*, 21(4): 339-345 (2005).

Shimmura et al., "Deep Lamellar Keratoplasty (DLKP) in Keratoconus Patients Using Viscoadaptive Viscoelastics," *Cornea*, 24(2): 178-181 (2005).

Stepp, "Corneal integrins and their functions," *Exp. Eye Res.*, 83(1): 3-15 (2006).

Takács et al., "Stem Cells of the Adult Cornea: From Cytometric Markers to Therapeutic Applications," *Cytometry Part A*, 75(1): 54-66 (2009).

Toma et al., "Isolation of multipotent adult stem cells from the dermis of mammalian skin," *Nat. Cell. Biol.*, 3(9): 778-784 (2001).

Yoshida et al., "Isolation of Multipotent Neural Crest-Derived Stem Cells from the Adult Mouse Cornea," *Stem Cells*, 24(12): 2714-2722 (2006).

Yoshida et al., "Generation of Stratified Squamous Epithelial Progenitor Cells from Mouse Induced Pluripotent Stem Cells," *PLoS One*, 6(12): e28856 (2011).

European Patent Office, Supplementary European Search Report in European Patent Application No. 12837799 (dated Oct. 7, 2015).

European Patent Office, Communication Pursuant to Rule 164(1) EPC in European Patent Application No. 15867053.9 (dated Jul. 30, 2018).

Japanese Patent Office, International Search Report in International Patent Application No. PCT/JP2012/076048 (dated Jan. 8, 2013).

Kim et al., "Efficacy of the soft-shell technique using Viscoat and Hyal-2000," *J. Cataract Refract. Surg.*, 30(11): 2366-2370 (2004).

Parekh et al., "Reconstructions and Regeneration of Corneal Endothelium: A Review on Current Methods and Future Aspects," *J. Cell Sci. Ther.*, 4(3): 1000146 (2013).

European Patent Office, Extended European Search Report in European Patent Application No. 15867053.9 (dated Nov. 7, 2018).

* cited by examiner

\*\*; p<0.01,
multiple t-test with Bonferroni correction following ANOVA verification of EMT alpha-SMA (immunostaining)

α-SMA positive cell was not observed verification of cell form (cytoskeleton)

F-actin (Phalloidin staining)

Circumferential actin fiber formation

METHOD FOR PRODUCING THERAPEUTIC CORNEAL ENDOTHELIAL SUBSTITUTE CELL SPHERE

CROSS-REFERENCE TO RELATED APPLICATIONS

This patent application is the U.S. national phase of International Patent Application Ser. No. PCT/JP2015/084857, filed on Dec. 11, 2015, which claims the benefit of Japanese Patent Application No. 2014-251236, filed Dec, 11, 2014, the disclosures of which are incorporated herein by reference in their entireties for all purposes.

TECHNICAL FIELD

The present invention relates to a method of producing a therapeutic alternative corneal endothelial cell from a stem cell, particularly, a method of inducing a stem cell into a therapeutic alternative corneal endothelial cell via a cell aggregate (sphere) by suspension culture. Furthermore, the present invention relates to a pharmaceutical composition for transplantation, which contains a sphere of therapeutic alternative corneal endothelial cells, and a pharmaceutical composition for transplantation, which contains cultured corneal endothelial cells.

BACKGROUND ART

The visual information is recognized when the light that entered from the cornea, which is a transparent tissue on the frontmost surface of the eyeball, reaches the retina to excite the retinal nerve cell, and the developed electric signals reach the visual field in the cerebrum via optic nerve. In other words, the cornea is positioned in front of a path where the light passes when a living organism receives visual information. Therefore, the turbidity in the cornea caused by damage and the like has a serious influence on the visual function.

Histologically, the cornea has a three-layer structure of corneal epithelium, corneal stroma, and corneal endothelium from the outer surface side. The transparency of cornea is maintained since the water content is kept constant by $Na^+$ active transport (pump function) by Na, K-ATPase and barrier function (tight junction protein such as ZO-1 and the like) in the corneal endothelium.

The above-mentioned function of corneal endothelial cell is impaired by a damage to the corneal endothelium such as a decrease in the corneal endothelial cell and the like, thus resulting in the edema of the corneal stroma. This decreases transparency of the cornea, and reduces the visual acuity. Such condition is called bullous keratopathy. In the meantime, it is known that human corneal endothelial cell once injured scarcely shows an ability to regenerate. When the corneal endothelial cells have decreased due to certain injury, an effective or, in some cases, sole treatment thereof is corneal transplantation. In fact, about half the number of applicable cases of corneal transplantation is for bullous keratopathy caused by corneal endothelial functional disorder.

At present, patients with corneal endothelium damage are treated by penetrating keratoplasty wherein the whole three-layer structure of corneal epithelium, corneal stroma and corneal endothelium is transplanted. While the penetrating keratoplasty is an established technique, the supply of cornea is short in Japan as the situation stands, and the rejection reaction poses a problem. To solve such problems, "part transplantation" involving transplantation of only the damaged tissue is becoming popular. Deep lamellar keratoplasty (DLKP) involving transplantation of only the epithelium and stroma of the donor while preserving corneal endothelium (non-patent documents 1 and 2), corneal endothelium transplantation involving transplantation of only the part cornea including endothelium (patent documents 1 and 2, non-patent document 3) and the like are known. However, in the case of corneal endothelium transplantation, for example, the source of supply of the material for transplantation is still the corneal endothelium itself. Since the number of donor of cornea is limited, the problem of donor shortage cannot be overcome, like penetrating keratoplasty. Furthermore, since corneal endothelial cell is difficult to culture, preparation of cultured cells in a number sufficient for transplantation places a large burden in terms of time and cost.

The present inventors have reported a method of differentiation induction of corneal endothelial cells from stem cells such as iPS cell (induced pluripotent stem cell) and the like (patent document 3), and a method of producing a single layer cell sheet of corneal endothelial cells from stem cells such as iPS cell and the like (patent document 4).

On the other hand, a method of forming cell aggregates from iris parenchymal tissue and differentiating same into corneal endothelial cells (patent document 5) and an attempt to culture human cultured corneal endothelial cells in the state of cell aggregates (patent document 6) have been reported.

DOCUMENT LIST

Patent Documents patent document 1: JP-A-2004-24852
patent document 2: JP-A-2005-229869
patent document 3: WO 2013/051722
patent document 4: JP application No. 2013-150993
patent document 5: JP-A-2009-268433
patent document 6: JP-A-2006-187281

Non-Patent Document non-patent document 1: Aggarwal R K. Br J Ophthalmol 1997; 81:178-179.
non-patent document 2: Shimmura S. et al., Cornea 2005; 24(2):178-81.
non-patent document 3: Price F W Jr, Price M O. J Refract Surg. 2005; 21(4):339-45.

SUMMARY OF THE INVENTION

Problems to be Solved by the Invention

An object of the present invention is to stably produce a large amount of therapeutic alternative corneal endothelial cell capable of treating corneal endothelium functional disorder, which is an alternative cell to a corneal endothelial cell, in a state suitable for intraocular (into anterior chamber) transplantation. Furthermore, the present invention aims to provide a composition for transplantation, which contains therapeutic alternative corneal endothelial cells obtained by the method of the present invention.

Means of Solving the Problems

In view of the above-mentioned problem, the present inventors have conducted intensive studies and found that, by forming a cell aggregate (sphere) by culturing stem cells in suspension under particular differentiation induction conditions, and using the sphere for transplantation, a tissue to be an alternative to a corneal endothelial cell layer can be constructed rapidly after the transplantation and superior corneal endothelial function can be obtained, which resulted in the completion of the present invention.

Therefore, the present invention provides the following.

[1] A method of producing a sphere of therapeutic alternative corneal endothelial cells, comprising culturing stem cells in suspension in a differentiation induction medium, wherein the differentiation induction medium comprises a GSK3 inhibitor, retinoic acid and a ROCK inhibitor.
[2] The method of the above-mentioned [1], wherein the differentiation induction medium further comprises an N2 supplement, EGF and bFGF.
[3] The method of the above-mentioned [1], wherein the GSK3 inhibitor is (2'Z,3'E)-6-bromoindirubin-3'-oxime (BIO).
[4] The method of the above-mentioned [1], wherein the ROCK inhibitor is (+)-(R)-trans-4-(1-aminoethyl)-N-(4-pyridyl)cyclohexanecarboxamide dihydrochloride (Y-27632).
[5] The method of the above-mentioned [1], wherein the retinoic acid is all-trans-retinoic acid.
[6] The method of any of the above-mentioned [1] to [5], wherein the stem cell is an iPS cell-derived neural crest stem cell or a corneal stroma-derived neural crest stem cell.
[7] The method of the above-mentioned [6], wherein the stem cell is an iPS cell-derived neural crest stem cell.
[8] The method of any of the above-mentioned [1] to [5], wherein the stem cell is a skin-derived pluripotent progenitor cell.
[9] A sphere of therapeutic alternative corneal endothelial cells, which is obtained by the production method of any of the above-mentioned [1] to [8].
[10] The sphere of the above-mentioned [9], which is for transplantation.
[11] The sphere of the above-mentioned [10], which is for transplantation into anterior chamber.
[12] A pharmaceutical composition for transplantation comprising a sphere of therapeutic alternative corneal endothelial cells, and a viscoelastic substance.
[13] A pharmaceutical composition for transplantation comprising a cultured corneal endothelial cell, and a viscoelastic substance.
[14] The pharmaceutical composition of the above-mentioned [12] or [13], which is for transplantation into anterior chamber.
[15] The pharmaceutical composition of any of the above-mentioned [12]-[14], wherein the sphere of therapeutic alternative corneal endothelial cells is obtained by the production method of any of the above-mentioned [1]-[8].
[16] The pharmaceutical composition of any of the above-mentioned [12]-[14], wherein the cultured corneal endothelial cells are dispersed into single cells.
[17] The pharmaceutical composition of any of the above-mentioned [12]-[16], wherein the viscoelastic substance is hyaluronic acid and/or chondroitin sulfate.
[18] The pharmaceutical composition of the above-mentioned [17], wherein the hyaluronic acid has a concentration of 5-40 mg/ml.
[19] The pharmaceutical composition of the above-mentioned [17] or [18], wherein the chondroitin sulfate has a concentration of 5-50 mg/ml.
[20] The pharmaceutical composition of any of the above-mentioned [12]-[19], further comprising retinoic acid and a ROCK inhibitor.
[21] The pharmaceutical composition of the above-mentioned [20], further comprising insulin, EGF and bFGF.

Effect of the Invention

According to the present invention, a therapeutic alternative corneal endothelial cell can be produced more efficiently from a stem cell. Since a sphere of therapeutic alternative corneal endothelial cells produced by the present invention maintains intercellular tight junctions, when the sphere is directly transplanted by injecting into the anterior chamber, a corneal endothelium tissue can be constructed rapidly after the transplantation, and epithelial-mesenchymal transition (EMT) can be prevented.

In addition, administration of a sphere of therapeutic alternative corneal endothelial cells as the pharmaceutical composition of the present invention enables efficient retention and adhesion of the therapeutic alternative corneal endothelial cells to the transplantation site.

According to the present invention, transplantation by administration of a sphere of therapeutic alternative corneal endothelial cells or cultured corneal endothelial cells into the anterior chamber together with a viscoelastic substance such as hyaluronic acid, chondroitin sulfate and the like enables efficient retention and adhesion of the cells thereof to the transplantation site.

DESCRIPTION OF EMBODIMENTS

Figure 1:
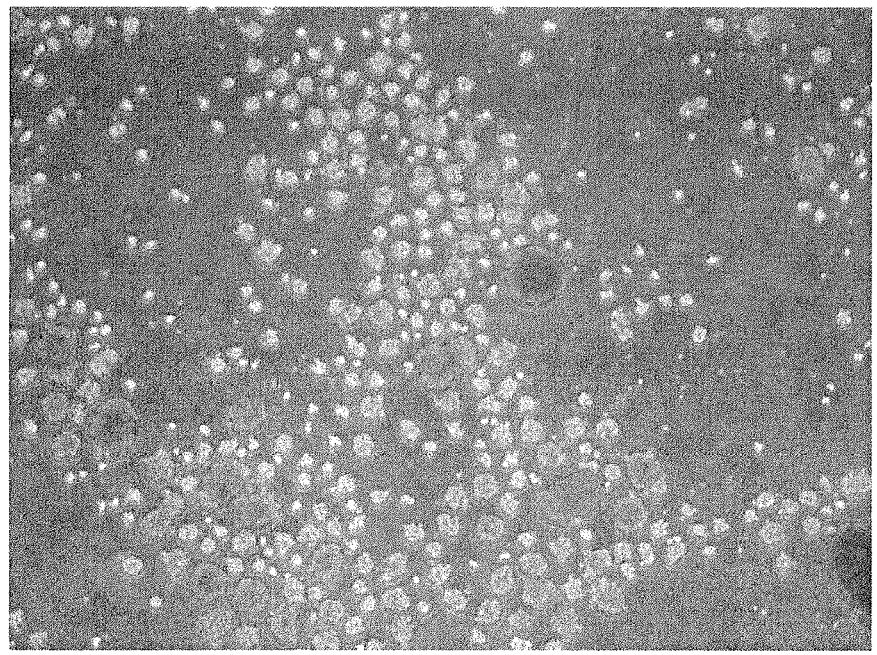
FIG. 1 shows a microscopic photograph of therapeutic alternative corneal endothelial cell sphere produced from human iPS cell-derived neural crest stem cells by suspension culture.

The present invention is explained in the following. Unless particularly indicated, the terms used in the present specification have the meanings generally used in the pertinent field.

In the present invention, the "stem cell" means a cell capable of being cultured in vitro, and capable of differentiating into plural lines of cells constituting the body. Among others, it means a cell capable of differentiating into a corneal endothelial cell. Specific examples include embryonic stem cell (ES cell), embryonic primordial germ cell-derived pluripotent stem cell (EG cell), testis-derived pluripotent stem cell (GS cell), somatic cell-derived artificial pluripotent stem cell (induced pluripotent stem cells; iPS cell), human somatic stem cell (tissue stem cell), and those capable of being induced to differentiate into a corneal endothelial cell. More preferred are an iPS cell-derived neural crest stem cell and a corneal stroma-derived neural crest stem cell. The neural crest stem cell is a pluripotent stem cell having a self-replication ability and multipotency, and is known to move from the back side of the neural tube into the whole body during the developmental process of vertebrate animals to contribute to the formation of various tissues. The corneal endothelium is considered to derive from neural crest, like corneal stroma.

As the ES cell, an ES cell derived from any warm-blooded animal, preferably a mammal, can be used. Examples of the mammal include mouse, rat, guinea pig, hamster, rabbit, cat, dog, sheep, swine, bovine, horse, goat, monkey, human and the like. A cell derived from human can be preferably used.

Specific examples of the ES cell include an ES cell of a mammal and the like, which is established by cultivating an early embryo before implantation, an ES cell established by cultivating an early embryo produced by nuclear transplantation of the nucleus of a somatic cell, and an ES cell wherein a gene on the chromosome of such ES cell is altered by a genetic engineering method. Each ES cell can be prepared by a method generally performed in the field, or according to known documents.

As the iPS cell, an iPS cell derived from any warm-blooded animal, preferably a mammal, can be used. Examples of the mammal include mouse, rat, guinea pig, hamster, rabbit, cat, dog, sheep, swine, bovine, horse, goat, monkey, human and the like. A cell derived from human can be preferably used.

Specific examples of the iPS cell include cells obtained by introducing plural genes into a somatic cell such as skin cell and the like, which have acquired multipotency same as that of ES cell. Examples thereof include iPS cell obtained by introducing Oct3/4 gene, Klf4 gene, C-Myc gene and Sox2 gene, iPS cell obtained by introducing Oct3/4 gene, Klf4 gene and Sox2 gene (Nat Biotechnol 2008; 26: 101-106) and the like. Furthermore, the production method of iPS cell has been intensively improved technically, for example, a method involving further reducing transgenes (Nature. 2008 Jul. 31; 454(7204): 646-50), a method utilizing a low-molecular-weight compound (Cell Stem Cell. 2009 Jan. 9; 4(1): 16-9, Cell Stem Cell. 2009 Nov. 6; 5(5): 491-503), a method utilizing a transcription factor protein instead of the gene (Cell Stem Cell. 2009 May 8; 4(5): 381-4) and the like. Since the basic property of the iPS cells produced, that is, having multipotency, is equivalent irrespective of the production methods, all of them can be used as the method of the present invention.

In the present invention, an iPS cell-derived neural crest stem cell is more preferably used. Using the neural crest stem cell, induction of differentiation into a therapeutic alternative corneal endothelial cells is facilitated. The neural crest stem cell can be induced from an iPS cell according to a method known in the field, or a method analogous thereto. For example, the induction can be performed according to the method described in Nature Protocols, 2010 vol. 5, No. 4, 688-701 or Nature, 2010 vol. 463, 958-964.

As the somatic stem cell, a somatic stem cell derived from human can be used. The somatic stem cell here is a cell capable of being differentiated into a corneal endothelial cell and, for example, corneal stroma-derived neural crest stem cell (Corneal-derived progenitors: COPs), mesenchymal stem cell (mesenchymal stem cells), skin-derived pluripotent progenitor cell (skin-derived precursors: SKPs) and the like can be mentioned. Preferred are COPs and SKPs. COPs can be prepared by, for example, the method described in Stem Cells. 2006; 24(12):2714-2722. Specifically, they are prepared by treating corneal stroma, which obtained by removing epithelium and endothelium from mouse cornea with collagenase, and culturing the separated cells in a DMEM/F12 medium added with EGF (Epidermal Growth Factor), FGF2 (Fibroblast Growth Factor 2), B27 supplement and LIF (Leukemia Inhibitory Factor). SKPs can be prepared according to, for example, the method described in Nat Cell Biol., 2001 vol. 3, 778-784.

1. Production Method of Therapeutic Alternative Corneal Endothelial Cell Sphere

The production method of the present invention is a method for producing a therapeutic alternative corneal endothelial cell sphere from stem cells, and includes a step of culturing stem cells in suspension in a differentiation induction medium having a particular composition.

In the present invention, the "therapeutic alternative corneal endothelial cell" is a cell induced from a stem cell such as iPS cell and the like, and can treat a corneal endothelium functional disorder and replace corneal endothelial cells.

That is, the therapeutic alternative corneal endothelial cell has physiological functions equivalent to those of the corneal endothelial cell.

The therapeutic alternative corneal endothelial cell sphere produced by the production method of the present invention (hereinafter to be also referred to as the sphere of the present invention) is a cell mass formed by aggregation of several dozen to several hundred cells, and generally has a spherical shape. As used herein, "spherical" includes a complete sphere, as well as substantially spherical shapes such as an egg shape and a rugby ball shape.

The sphere preferably has a diameter of, for example, 20-2000 μm, more preferably 30-1500 μm, particularly preferably 40-1000 μm.

The differentiation induction medium to be used in the production method of the present invention (hereinafter to be also referred to as the differentiation induction medium of the present invention) contains a GSK3 (Glycogen synthase kinase 3) inhibitor, retinoic acid and a ROCK (Rock kinase) inhibitor.

The stem cell to be used in this step is as mentioned above. It is preferably a cell destined to differentiate into a corneal endothelial cell, specifically an iPS cell-derived neural crest stem cell or a corneal stroma-derived neural crest stem cell (COPs). Use of a skin-derived pluripotent progenitor cell (SKPs) is also preferable. For example, when a more undifferentiated stem cell such as iPS cell, ES cell and the like is used, a step for induction into a neural crest stem cell can be or is preferably performed before the above-mentioned step. Such step can be performed by, for example, the method described in Nature Protocols, 2010, vol. 5, No. 4, 688-701 or a method analogous thereto.

GSK3 (glycogen synthase kinase 3), which is a serine/threonine protein kinase, is involved in many signal pathways relating to glycogen production, apoptosis, maintenance of stem cell and the like. GSK3 includes isoforms (GSK3α and GSK3β) encoded by different genes and having high homology at the amino acid level. In addition, it is known that GSK3β is also involved in Wnt signal, and inhibition of GSK3β activates Wnt signal. Examples of the GSK3 inhibitor include GSK3α inhibitor and GSK3β inhibitor. Specific examples of the GSK3 inhibitor include CHIR98014, CHIR99021, Kenpaullone, AR-AO144-18, TDZD-8, SB216763, BIO ((2'Z,3'E)-6-Bromoindirubin-3'-oxime), TWS-119, SB415286, Ro3303544 and the like. All of these are commercially available, or can also be prepared by those of ordinary skill in the art, by reference to known documents. In this step, BIO is preferably used. The concentration of the GSK3 inhibitor in a medium is appropriately determined according to the kind of the inhibitor to be used. In the case of BIO, the concentration is generally 10-1000 nM, preferably 50-1000 nM, more preferably about 500 nM. One or more kinds of GSK3 inhibitors may be used in combination.

Examples of the retinoic acid to be used in this step include all-trans-retinoic acid (ATRA), 9-cis-retinoic acid, 11-cis-retinoic acid, 13-cis-retinoic acid and the like. All of these are commercially available, or can also be prepared by those of ordinary skill in the art, by reference to known documents. In this step, it is preferably all-trans-retinoic acid. The concentration of the retinoic acid in a medium is appropriately determined according to the kind of the retinoic acid to be used. The concentration of all-trans-retinoic acid in a medium is generally 1-1000 nM, preferably 10-1000 nM, more preferably about 100 nM. In the pharmaceutical composition of the present invention, retinoic acid may be esterified with a fatty acid. In the case of medical retinol palmitate, it is used at generally about 2-200 unit/ml, preferably about 40-150 unit/ml, more preferably about 100-120 unit/ml.

The ROCK inhibitor refers to a substance that inhibits the activity of Rho kinase. The Rho kinase is one kind of low-molecular-weight GTP binding protein (low molecular weight G protein) included in the category of GTPase, which is a degrading enzyme of GTP (guanosine triphosphate), and has a serine/threonine kinase region in the amino terminal, a coiled coil region in the center, and a Rho interaction region in the carboxy terminal.

Examples of the ROCK inhibitor to be used in this step include 1-(5-isoquinolinesulfonyl)-2-methylpiperazine (H-7), 1-(5-isoquinolinesulfonyl)-3-methylpiperazine (iso H-7), N-2-(methylamino)ethyl-5-isoquinolinesulfoneamide dihydrochloride (H-8), N-(2-aminoethyl)-5-isoquinolinesulfoneamide dihydrochloride (H-9), N-[2-(p-bromocinnamylamino)ethyl]-5-isoquinolinesulfoneamide dihydrochloride (H-89), N-(2-guanidinoethyl)-5-isoquinolinesulfoneamide hydrochloride (HA-1004), 1-(5-isoquinolinesulfonyl)homopiperazine dihydrochloride (Fasudil/HA-1077), (S)-(+)-2-methyl-4-glycyl-1-(4-methylisoquinolinyl-5-sulfonyl)homopiperidine dihydrochloride (H-1152), and (+)-(R)-trans-4-(1-aminoethyl)-N-(4-pyridyl)cyclohexanecarboxamide dihydrochloride (Y-27632).

All of these are commercially available, and Y-27632 is particularly preferable. The concentration of the ROCK inhibitor in a medium is appropriately determined according to the kind of the inhibitor to be used. In the case of Y-27632, the concentration is generally 5-20 μM, preferably about 10 μM. One or more kinds of the ROCK inhibitors may be used in combination.

The differentiation induction medium of the present invention may further contain, and preferably contain, N2 supplement, EGF and bFGF (Basic Fibroblast Growth Factor), in addition to the above-mentioned GSK3 inhibitor, retinoic acid and ROCK inhibitor.

N2 supplement is a serum replacement widely used for culturing nerve system cells, and is a commercially available reagent containing insulin, transferrin, progesterone, putrescine and sodium selenite. It can be used at a general concentration used for cell culture and, for example, commercially available N2 supplement is added according to the manual thereof.

EGF (epidermal growth factor) is a protein consisting of 53 amino acid residues and three intramolecular disulfide bonds. It binds as a ligand to EGFR (epidermal growth factor receptor) present on the cellular surface, and plays an important role in the control of the cell growth and proliferation. The derivation of EGF to be used in the present invention is not particularly limited as long as it is effective for the production of the sphere of the present invention. In consideration of intraocular application in the future, however, it is preferably derived from human. EGF is commercially available, or can also be prepared by those of ordinary skill in the art, by reference to known documents. For example, it can be synthesized based on known base sequences and amino acid sequences. The concentration of EGF in a medium is generally 1-100 ng/ml, preferably about 20 ng/ml.

bFGF (basic fibroblast growth factor) is one kind of protein inherently present in the body, and is known to control cell growth and differentiation, and have functions such as angiogenesis, smooth muscle cell proliferation, wound therapy, tissue repair, hematopoiesis, nerve cell differentiation and the like in various tissues and organs. The derivation of bFGF to be used in the present invention is not particularly limited as long as it is effective for the production of the sphere of the present invention. In consideration of intraocular application in the future, however, it is preferably derived from human. bFGF is commercially available, or can also be prepared by those of ordinary skill in the art, by reference to known documents. For example, it can be synthesized based on known base sequences and amino acid sequences. The concentration of bFGF in a medium is generally 1-50 ng/ml, preferably about 20 ng/ml.

In this step, respective components in the differentiation induction medium (hereinafter to be also referred to as the addition factor of the present invention) may be simultaneously added to a medium, or may be separately added to a medium in a staggered manner as long as the therapeutic alternative corneal endothelial cell sphere can be induced from a stem cell. It is convenient and preferable to simultaneously add each addition factor to a medium. A monolayer cell layer of therapeutic alternative corneal endothelial cells extends from the sphere by adhesion culture of the formed sphere. For differentiation induction during adhesion culture, the medium is preferably exchanged with a medium free of a GSK3 inhibitor.

The medium to be used in this step is not particularly limited as long as it contains the above-mentioned each addition factor, and is generally a medium used for cultivating stem cells (hereinafter to be also referred to as a basal medium for convenience) and added with each addition factor. The basal medium is not particularly limited as long as it can be used for culturing animal cells, and includes, for example, MEM (Minimum Essential Medium) medium, BME (Basal Medium Eagle) medium, BGJb medium, CMRL 1066 medium, Glasgow MEM medium, Improved MEM Zinc Option medium, IMDM (Iscove's Modified Dulbecco's Medium) medium, Medium 199 medium, Eagle MEM medium, αMEM medium, DMEM (Dulbecco's Modified Eagle's Medium) medium, ham medium, RPMI (Roswell Park Memorial Institute medium) 1640 medium, Fischer's medium, F12 medium and a mixed medium thereof. These media are commercially available. Furthermore, the medium to be used in this step can be a serum-containing medium or serum-free medium. When the medium to be used in this step is a serum-containing medium, mammalian sera such as bovine serum, fetal bovine serum and the like can be used. The concentration of the serum in a medium is 0.1-20%, preferably 1-10%. It is preferably a serum-free medium, in which case a serum replacement is added.

The basal medium to be used in this step is preferably a mixed medium of DMEM medium and F12 medium.

Where necessary, the medium to be used in this step can contain vitamin, buffering agent, inorganic salts, antibiotic (e.g., penicillin, streptomycin) and the like.

This step is performed by culturing in suspension in a $CO_2$ incubator aerated with 1-10%, preferably 5%, carbon dioxide at a culture temperature suitable for culture of stem cells to be used, generally 30-40° C., preferably about 37° C., for a period sufficient for inducing a therapeutic alternative corneal endothelial cell sphere. When iPS cell-derived neural crest stem cells, COPs or SKPs are used as the stem cell, they are preferably cultured for 7 days to 2 weeks. When the culture period is too short, sphere formation may not be sufficient, and when it is too long, the sphere may become too large for treatment use. Where necessary, the medium is exchanged as appropriate (e.g., once every 3 days). As mentioned above, the kind (combination) of each addition factor to be added can be or is preferably changed as necessary. A sphere starts to form from about two days after the start of suspension culture.

As used herein, the "suspension culture" refers to culturing cells in the state of non-adhesion to the culture substrate. Culturing can be performed using, while not particularly limited, a culture substrate not applied with artificial treatment for improving adhesiveness to the cell (e.g., coating treatment with extracellular matrix and the like), or a culture substrate applied with artificial treatment for suppressing adhesion of cells (e.g., coating treatment with 2-methacryloyloxyethylphosphoryl choline (MPC)). Examples of the culture substrate include dish, petri dish, plate (microtiter plate, microplate, deepwell plate etc. such as 6 well, 24 well and the like), flask, tube, roller bottle, spinner flask and the like. These culture substrates may be composed of either an inorganic material such as glass and the like or an organic material such as polystyrene and the like.

In this step, production of a therapeutic alternative corneal endothelial cell sphere from a stem cell can be confirmed by visual observation under a microscope. In addition, since a tight junction is formed at the cell boundary in the sphere of the present invention, the production can be confirmed by examining the protein level or gene level expression of a molecule specific to the tight junctions at the cell boundary. The expression of the protein can be evaluated by a method utilizing an antigen antibody reaction and the like, and the expression of the gene can be evaluated by a method utilizing RT-PCR and the like. Examples of the marker include ZO-1, CLDN7 and the like.

A layer of therapeutic alternative corneal endothelial cell can be produced by adhesion culture of the formed therapeutic alternative corneal endothelial cell sphere as it is. The therapeutic alternative corneal endothelial cell layer spreads on the culture substrate from the adhesion cultured sphere. The cell layer that has spread from the sphere also maintains tight junctions, and an adhesive junction by N-cadherin, which is characteristic of corneal endothelial cell, can be formed. The cell also has $Na^+,K^+$-ATPase pumping function. The adhesive junction by N-cadherin can be confirmed by examining expression at a protein level (e.g., method utilizing antigen antibody reaction) or gene level (e.g., method utilizing RT-PCR). The $Na^+, K^+$-ATPase pumping function of the cell can be measured, for example, according to the methods described in Investigative Ophthalmology & Visual Science, 2010 vol. 51, No. 8, 3935-3942, and Current Eye Research, 2009 vol. 34, 347-354 and using the Ussing chamber.

Conveniently, differentiation induction into therapeutic alternative corneal endothelial cell layer can also be confirmed by evaluating the cell morphology. A cell differentiated into an endothelial cell shows a mosaic growth form.

According to the present invention, a therapeutic alternative corneal endothelial cell sphere, which is a precursor state of a therapeutic alternative corneal endothelial cell layer, can be produced from iPS cell, skin stem cell, and various other somatic stem cells by suspension culture. Since the sphere maintains intercellular tight junction, it can be and is preferably transplanted by direct injection into the anterior chamber.

2. Pharmaceutical Composition

The present invention provides a pharmaceutical composition containing a therapeutic alternative corneal endothelial cell sphere and a viscoelastic substance, particularly a pharmaceutical composition for transplantation. Furthermore, the present invention provides a pharmaceutical composition containing cultured corneal endothelial cells and a viscoelastic substance, particularly a pharmaceutical composition for transplantation. In the present specification, these are sometimes to be comprehensively abbreviated as the pharmaceutical composition of the present invention. The pharmaceutical composition is preferably used for intraocular transplantation of therapeutic alternative corneal endothelial cells or cultured corneal endothelial cells, particularly transplantation into the anterior chamber. Since the composition contains a viscoelastic substance, the spheres and cells can be efficiently adhered to the site in need of transplantation, without diffusion thereof.

As the therapeutic alternative corneal endothelial cell sphere, those produced by the above-mentioned "1. Production method of therapeutic alternative corneal endothelial cell sphere" can be mentioned.

While the cultured corneal endothelial cells may be primary cultured cells or established line of cells, established line of cells are preferably used since primary culture of corneal endothelial cells is difficult. While the cultured corneal endothelial cells are preferably dispersed into single cells, as long as adhesion to the cornea is possible, they can also be used in the form of a cell aggregate of 2—several cells, 10—several dozen cells, and the like as necessary.

While the "viscoelastic substance" is not particularly limited as long as it can impart appropriate viscosity to a solution for transplantation containing a sphere or cell (hereinafter sometimes to be abbreviated as solution for transplantation), preferred are/is hyaluronic acid and/or chondroitin sulfate, more preferred are hyaluronic acid and chondroitin sulfate. These components are substances generally utilized in an ophthalmic field, and can be used without the fear of side effects.

Hyaluronic acid and chondroitin sulfate can also be used in the form of salt or ester. For example, since hyaluronic acid is commercially available as sodium hyaluronate, and chondroitin sulfate is commercially available as chondroitin sulfate ester sodium (e.g., viscoat (registered trade mark) 0.5; containing sodium hyaluronate at a concentration of 30 mg/ml and chondroitin sulfate ester sodium at a concentration of 40 mg/ml), they can be used conveniently.

The hyaluronic acid concentration is generally 5-40 mg/ml, preferably 10-30 mg/ml, more preferably 15-25 mg/ml.

The chondroitin sulfate concentration is generally 5-50 mg/ml, preferably 15-40 mg/ml, more preferably 20-35 mg/ml.

When viscoat (registered trade mark) 0.5 is used as a viscoelastic substance, it is mixed with a solution for transplantation containing sphere or cell, at a ratio of viscoat: solution for transplantation of 1:1-5, preferably 1:1-3. When the solution for transplantation is too much, sufficient viscosity cannot be obtained, sufficient retention of administered sphere or cell in the transplantation site is prevented, and the sphere or cell may leak out from wound immediately after injection. When the viscoelastic substance is too much, the intraocular pressure is feared to rise.

While the solution for transplantation is not particularly limited as long as it is a solution suitable for intraocular administration, particularly administration into the anterior chamber, a nonirritating isotonized culture medium, saline, buffer and the like are used. Preferably, a culture medium similar to one used for culturing the therapeutic alternative corneal endothelial cell sphere or cultured corneal endothelial cells is used. The pharmaceutical composition can contain various components as necessary. While the component is not particularly limited as long as it is useful for differentiation of the therapeutic alternative corneal endothelial cell sphere or cultured corneal endothelial cells, administered (transplanted) into the anterior chamber, into each endothelial cell layer without falling off, it is preferable to add retinoic acid and a ROCK inhibitor. Also, insulin, EGF and bFGF are also preferable components to be added.

As the "retinoic acid", "ROCK inhibitor" and "bFGF", those similar to the examples shown in the above-mentioned "1. Production method of therapeutic alternative corneal endothelial cell sphere" are used. While the concentration of retinoic acid in the pharmaceutical composition is appropriately determined according to the kind of retinoic acid to be used, in the case of all trans-retinoic acid, it is generally 10-1000 nM, preferably 200-800 nM, more preferably about 500 nM. In the pharmaceutical composition of the present invention, retinoic acid may be esterified with a fatty acid, and medical retinol palmitate is used at generally 2-200 unit/ml, preferably 40-150 unit/ml, more preferably about 100-120 unit/ml. While the concentration of ROCK inhibitor in the pharmaceutical composition is appropriately determined according to the kind of inhibitor, in the case of Y-27632, it is generally 1-10 µM, preferably about 5 µM. The concentration of EGF in the pharmaceutical composition is generally 10-200 ng/ml, preferably about 75 ng/ml. The concentration of bFGF in the pharmaceutical composition is generally 0.5-10 ng/ml, preferably about 1.5 ng/ml. Use at about 5 ng/ml is also preferable.

Insulin is one kind of peptide, and any of insulin produced from the pancreas of an animal, for example, bovine or swine and insulin produced by gene recombination technique can be used. In consideration of intraocular application in the future, however, it is preferably derived from human. Insulin is commercially available, or can also be prepared by those of ordinary skill in the art, by reference to known documents. For example, it can be synthesized based on known base sequences or amino acid sequences. The concentration of insulin in the pharmaceutical composition is generally 1-10 µg/ml, preferably about 7.5 µg/ml. Use at about 5 µg/ml is also preferable.

While the cell density of the therapeutic alternative corneal endothelial cell sphere suspension in the pharmaceutical composition is not particularly limited as long as it is an amount sufficient for covering the detached area, engrafting without falling off after transplantation, and differentiating into a therapeutic alternative corneal endothelial cell layer, a concentration of generally $1-5 \times 10^6$ cells/ml, preferably $1.5 \times 10^6$ cells/ml, is employed. The cell density of the sphere suspension is determined by sampling a part of the sphere suspension, dispersing the cells into single cells by an enzyme treatment of the sphere in the sample, counting the cells in the sample and using the results thereof.

While the cell density of the cultured corneal endothelial cell suspension in the in the pharmaceutical composition is not particularly limited as long as it is an amount sufficient for covering the detached area and engrafting without falling off after transplantation, a concentration of generally $1-5 \times 10^6$ cells/ml, preferably $1.5 \times 10^6$ cells/ml, is employed. The cell density of the suspension is determined by sampling a part of the suspension, counting the cells in the sample and using the results thereof.

Examples of the subject of administration of the pharmaceutical composition for transplantation of the present invention include mammals such as mouse, rat, hamster, guinea pig, rabbit, cat, dog, bovine, horse, sheep, monkey, human and the like, and preferred is human.

While the dose of the pharmaceutical composition for transplantation of the present invention varies depending on the body weight, age, symptom and the like of the subject of administration, for example, 50-200 µl per eye is administered into the anterior chamber of human.

EXAMPLES

The present invention is described in detail in the following by referring to Examples, which are not to be construed as limitative. Unless particularly specified, the reagents and materials to be used are commercially available.

Example 1

Production and Functional Evaluation of Therapeutic Alternative Corneal Endothelial Cell Sphere 1. Preparation of human iPS cell-derived neural crest stem cell Based on a publication (Nature, 2010 vol. 463, 958-964), neural crest stem cells were obtained from human iPS cell. This Example is different from the above-mentioned publication in that suspension culture was employed without using Matrigel for culturing iPS cells. Suspension culture enabled more efficient induction of differentiation into neural crest stem cells (iPS-NCC). The human iPS cells used were 201B7 (provided by Prof. Shinya Yamanaka (Kyoto University) and Prof. Hideyuki Okano (Keio University)).

2. Production of Therapeutic Alternative Corneal Endothelial to Cell Sphere iPS-NCC obtained in the above-mentioned 1. was subjected to an enzyme treatment with Accutase to give single cells. The cells were cultured in a low adhesive plate (or dish) (Nunc, Corning etc.) at a cell density of $1 \times 10^4$-$10^5$ cells/cm$^2$.

The medium composition was DMEM/F12 added with N2 supplement (1×), EGF (20 ng/ml), bFGF (20 ng/ml), ATRA (100 nM), BIO (500 nM) and Y27632 (10 µM).

Formation of a sphere was confirmed on day 2 from the start of culture (FIG. 1).

3. Tight Junction of Therapeutic Alternative Corneal Endothelial Cell Sphere

Whether tight junction is formed at the cell boundary in the sphere obtained in the above-mentioned 2. was confirmed by examining the presence or absence of expression of ZO-1 and CLDN7 by the immunofluorescence staining method.

(1) ZO-1 Staining
primary antibody: ×200 dilution; goat anti-ZO-1 antibody (LS-BIO, #LS-B9774)
secondary antibody: ×200 dilution; Alexa Fluor 488-labeled Donkey anti-goat antibody (Life Technologies Corporation, #A11055)
(2) CLDN7 Staining
primary antibody: ×200 dilution; rabbit anti-CLDN7 antibody (Abcam #ab27487)
secondary antibody: ×200 dilution; Cy-3-labeled Donkey anti-rabbit antibody (Jackson Laboratory, #711-165-152)
(3) DAPI Staining (DOJINDO LABORATORIES, #D212)

Figure 2:
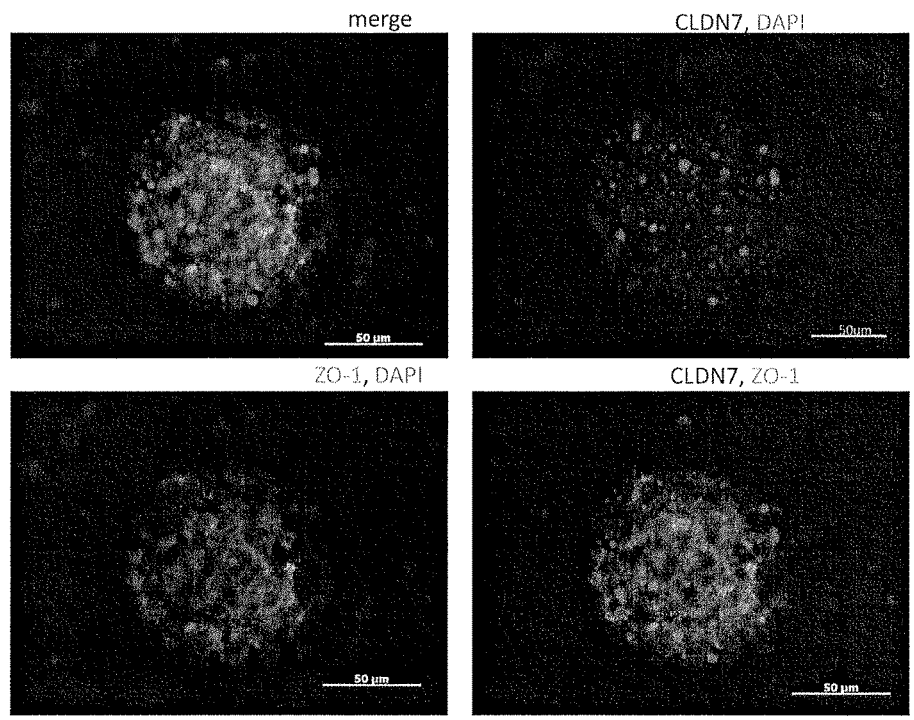
FIG. 2 shows formation of tight junction at the cell boundary in the sphere of the present invention. It is clear that ZO-1 and CLDN7 are expressed at the cell boundary.

The results are shown in FIG. 2. Expression of ZO-1 and CLDN7 was observed at the cell boundary. The results show that intercellular tight junction was already formed in the stage of spheres.

4. Functional Evaluation of Therapeutic Alternative Corneal Endothelial Cell Layer Produced from Therapeutic Alternative Corneal Endothelial Cell Sphere-1

Figure 3:
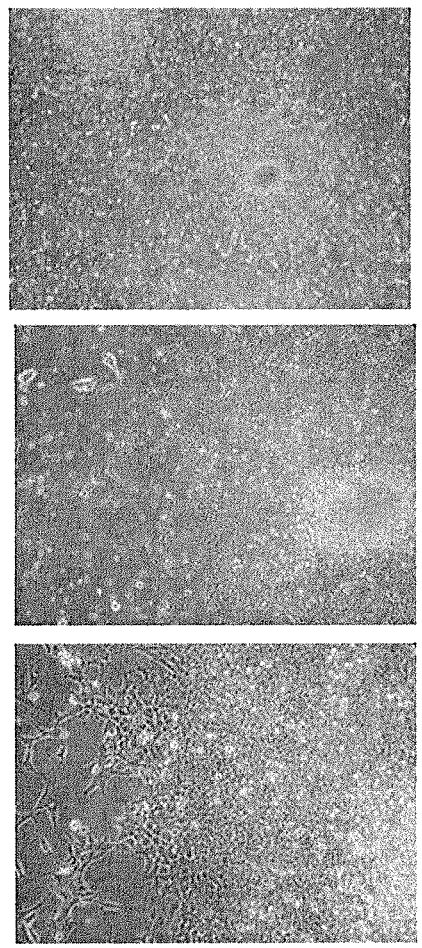
FIG. 3 shows spreading around of the cells from the sphere of the present invention when the sphere is cultured (adhesion culture) in a normal dish for adhesion culture. The figures have sequentially increasing magnifications.

The sphere obtained in the above-mentioned 2. was further cultured in suspension for not less than one week, and subjected to adhesion culture in a general dish for adhesion culture (IWAKI, #3000-035). As a result, the sphere adhered to the dish and the cells spread from the sphere (see FIG. 3). The cells that spread from the sphere were examined for expression of various proteins and functions. Specifically, expression of N-cadherin, which is characteristic of corneal endothelial cells, expression of ZO-1, which is characteristic of intercellular tight junction, and expression of Na,K-ATPase α1, which is important as the function of corneal endothelial cells were examined.

(1) ZO-1 Staining
primary antibody: ×100 dilution; rabbit anti-ZO-1 antibody (Invitrogen, #40-2200)
secondary antibody: ×200 dilution; Cy-3-labeled Donkey anti-rabbit antibody (Jackson Laboratory, #711-165-152)
(2) N-Cadherin Staining
primary antibody: ×100 dilution; mouse anti-N-cadherin antibody (Thermo Fisher Scientific, #MA1-2002)
secondary antibody: ×200 dilution; Alexa Fluor 488-labeled Donkey anti-mouse antibody (Life Technologies Corporation, #A21202)
(3) Na,K-ATPase α1 Staining
primary antibody: ×200 dilution; mouse anti-Na,K-ATPase α1 antibody (Novus biologicals, LLC., #NB300-146)
secondary antibody: ×200 dilution; Alexa Fluor 488-labeled Donkey anti-mouse antibody (Life Technologies Corporation, #A21202)

Figure 4:
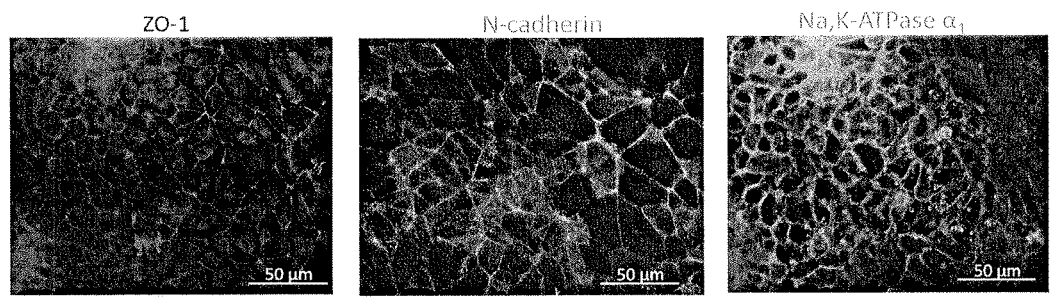
FIG. 4 shows formation of tight junction and adhesive junction at the cell boundary in a therapeutic alternative corneal endothelial cell derived from the sphere of the present invention. Expression of ZO-1 and N-cadherin was found at the cell boundary. Furthermore, expression of Na, K-ATPase was also confirmed on the cellular membrane.

The results are shown in FIG. 4. Expression of ZO-1 was observed at the cell boundary and it was confirmed that the tight junction structure was maintained (FIG. 4, left figure). Since expression of N-cadherin, which is characteristic of corneal endothelial cells, was observed, it was confirmed that an adhesive junction was also formed (FIG. 4, middle figure). Furthermore, Na,K-ATPase α1, which is important as the function of corneal endothelial cells, was also expressed along on the cellular membrane (FIG. 4, right figure).

Figure 5:
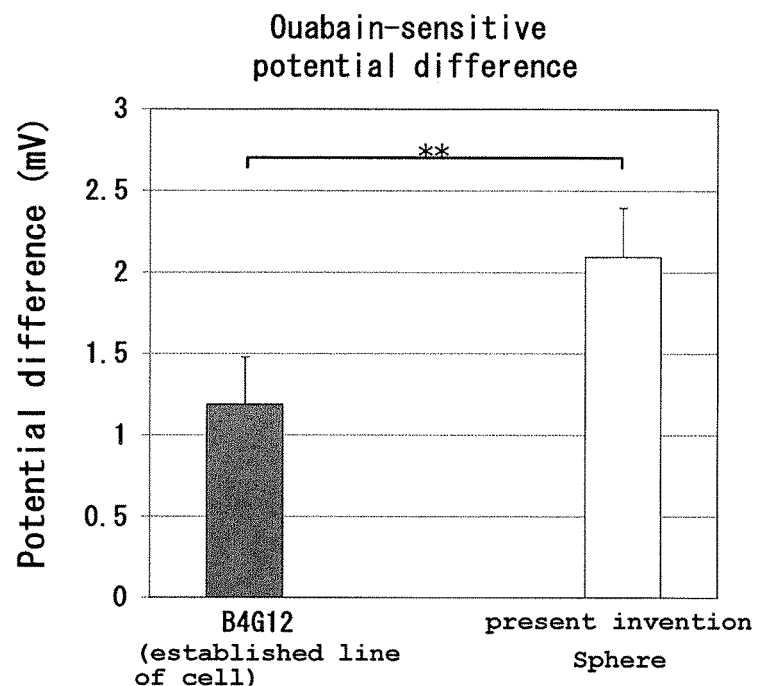
FIG. 5 is a graph showing that therapeutic alternative corneal endothelial cells derived from the sphere of the present invention show a sufficient pumping function. Pumping function was examined by voltage measurement using Ussing chamber. As the object, B4G12, which is an established line of corneal endothelial cell, was used.

The sphere obtained in the above-mentioned 2. was once sown again on a Snapwell (Corning, #3801), allowed to become confluent by culturing for 6 days, and inserted into Ussing chamber (Physiological Instrument; EM-CSYS-2). The short circuit currents (SCC) of the front and back of the wells were measured, and Na, K-ATPase pumping function was quantified from the difference in SCC before and after addition of 10 µM ouabain. As the control, Na, K-ATPase pumping function of B4G12 cell (DSMZ, #ACC-647), which is a human corneal endothelial cell line, was used. The results are shown in FIG. 5. The sphere of the present invention was found to have a pumping function equivalent to or not less than that of B4G12 cell, which is a human corneal endothelial cell line.

5. Functional Evaluation of Therapeutic Alternative Corneal Endothelial Cell Layer Produced from Therapeutic Alternative Corneal Endothelial Cell Sphere-2

When corneal endothelial cells in the state of a monolayer cell sheet are used for transplantation, generally, the cell sheet is treated with an enzyme to give single cells, which are injected as cell suspension into the anterior chamber and allowed to adhere to the posterior surface of the cornea. However, such an enzyme treatment is stressful for the cells, as a result of which the cells change into a mesenchymal cell form, thus problematically inducing epithelial-mesenchymal transition (EMT).

Whether EMT occurs even in the case via sphere as in the present invention was examined. Specifically, since change of expression marker from epithelial type to mesenchymal type and reconstruction of actin stress fiber are induced in the cell that acquired EMT, the presence or absence of expression of a mesenchymal cell marker (e.g., α-SMA, FSP-1), and the presence or absence of stress fiber formation were examined.
(1) α-SMA Staining
primary antibody: ×200 dilution; rabbit anti-α-SMA antibody (Bioss, #bs-0189R)
secondary antibody: ×200 dilution; Cy-3-labeled Donkey anti-rabbit antibody (Jackson Laboratory, #711-165-152)
(2) Actin Staining
×40 dilution; Alexa Fluor 488 Phalloidin (Invitrogen, #A12379)

Figure 6:
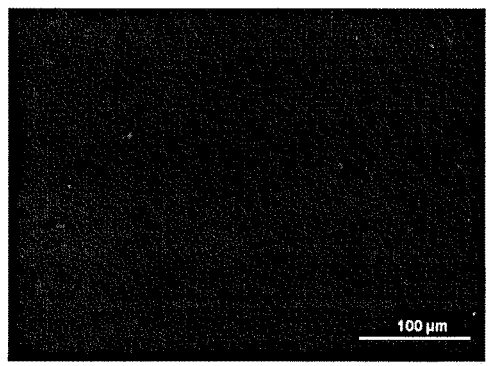
FIG. 6 verifies whether EMT is occurred in therapeutic alternative corneal endothelial cells derived from the sphere of the present invention. The left figure shows expression of α-SMA by immunofluorescent staining, and the right figure shows the presence or absence of stress fiber formation by actin staining with phalloidin.
Figure 6:
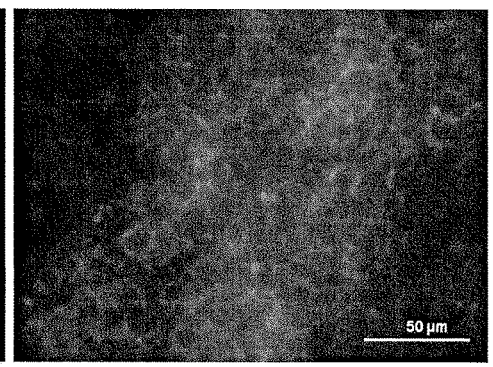

The results are shown in FIG. 6. α-SMA positive cell was not found and stress fiber was not formed in the therapeutic alternative corneal endothelial cell layer obtained from the sphere. These results show that EMT does not occur in the therapeutic alternative corneal endothelial cells obtained using the method via sphere of the present invention.

Example 2

Sphere Transplantation Experiment

1. Pharmaceutical Composition for Transplantation Containing Therapeutic Alternative Corneal Endothelial Cell Sphere Using the sphere obtained in the above-mentioned 2. and by the following procedure, a pharmaceutical composition for transplantation of the composition described in Table 1 was prepared.
(1) DMEM/F12 added with ATRA, Y27632, insulin and bFGF is prepared as a medium.
(2) Sphere is mixed with the medium obtained in (1) to a cell density of $1 \times 10^7$ cells/ml to give a cell suspension (×2).
(3) Viscoat (registered trade mark) 0.5 (200 μl) was added to and mixed with the cell suspension (200 μl) obtained in (2).

Viscoat (registered trade mark) 0.5 contains the Japanese Pharmacopoeia purified sodium hyaluronate (30 mg/ml), and chondroitin sulfate ester sodium (40 mg/ml).

TABLE 1

| (in DMEM/F12) | |
| --- | --- |
| sodium hyaluronate | 15 mg/ml |
| chondroitin sulfate ester sodium | 20 mg/ml |
| ATRA | 500 nM |
| Y27632 | 5 μM |
| insulin | 5 μg/ml |
| bFGF | 5 ng/ml |
| density of cell constituting sphere | $5 \times 10^6$ cells/ml |

2. Transplantation Of Sphere
(Procedure)

Using the pharmaceutical composition for transplantation prepared in the above-mentioned 1., a therapeutic alternative corneal endothelial cell sphere was transplanted into the ocular anterior chamber by the following procedure.
(1) While refluxing the anterior chamber of rabbit with saline, the endothelial side was rubbed to make the cells fall off.
(2) The anterior chamber after cell falling off was washed with saline.
(3) After washing, the pharmaceutical composition for transplantation prepared in the above-mentioned 1. was injected into the anterior chamber by using a 26 gauge syringe.

For comparison, an eye injected with a medium alone (Control; no sphere, without viscoat), and an eye injected only with a sphere and without using the pharmaceutical composition for transplantation (eye with sphere and without viscoat) were prepared.

(4) The rabbit was placed in a face-down position for 2 hr.
(5) After observation for 2 days, the eyeball was recovered and observed macroscopically and microscopically.

Similarly, a transplantation eye of *Macaca fascicularis* was also produced by injecting a sphere into the anterior chamber.

With respect to the transplantation eye, a formation of therapeutic alternative corneal endothelial cell layer and the corneal thickness and intraocular pressure were measured.

The corneal thickness was measured by a corneal thickness measuring apparatus (TOMEY CORPORATION; SP-100), and the intraocular pressure was measured by an intraocular pressure measuring apparatus (White Medical Co., Ltd.; AccuPen (manufactured by ACCUTOME)).
(Results)

Figure 7:
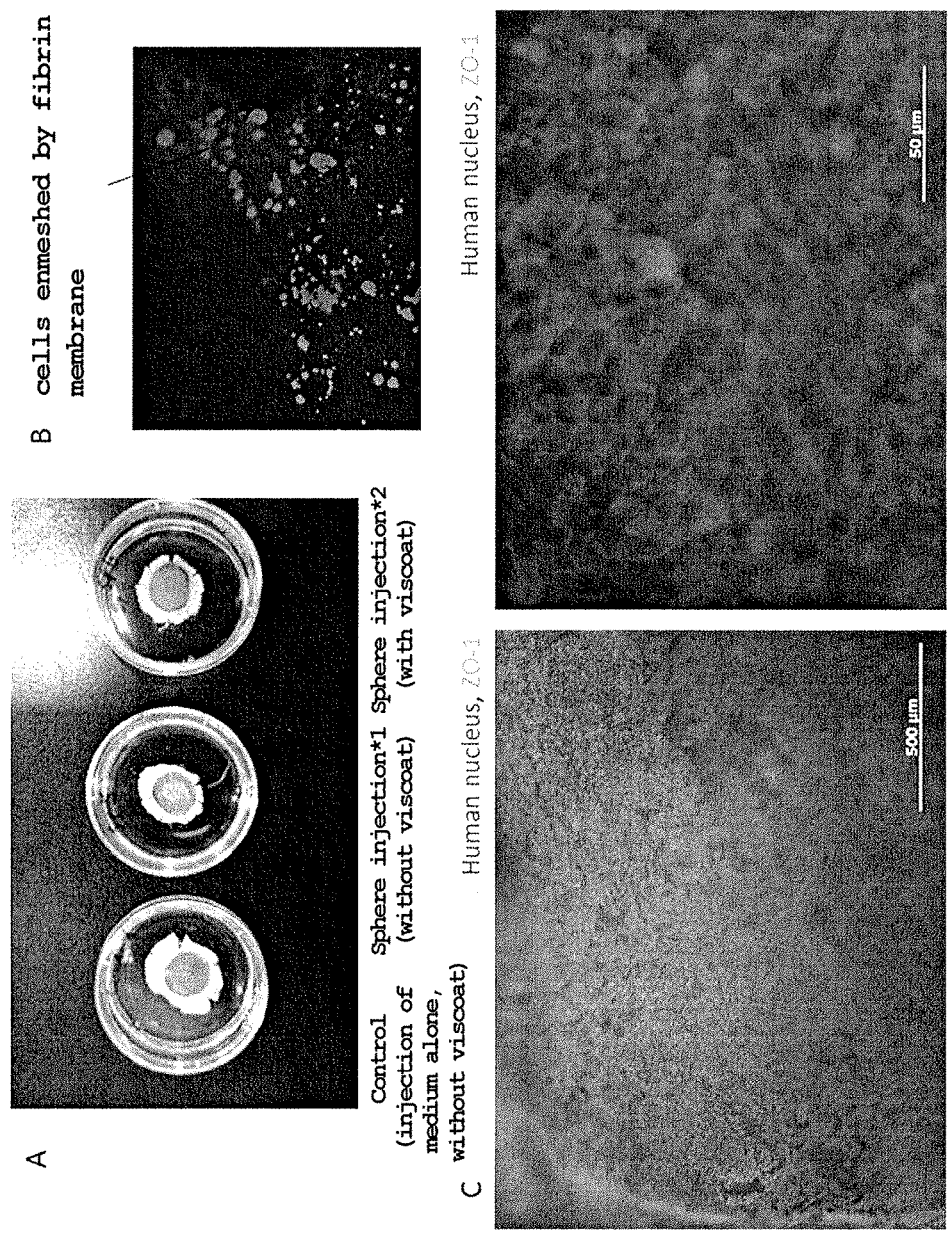
FIG. 7 shows the posterior surface of cornea of the transplanted eye on day 2 after injecting (transplanting) therapeutic alternative corneal endothelial cell sphere into the anterior chamber of a rabbit by using (or without using) the pharmaceutical composition for transplantation of the present invention containing the therapeutic alternative corneal endothelial cell sphere and a viscoelastic substance. When the pharmaceutical composition for transplantation of the present invention was used for injection, fibrin deposition was not observed (A, B), and it was shown that iPS-derived therapeutic alternative corneal endothelial cells, whose nucleus is stained with an anti-human nuclear antibody, spread and covered the posterior surface of cornea. Furthermore, formation of tight junction was maintained (C).

In the control and "eye with sphere and without viscoat" in the transplantation experiment of rabbit, fibrin deposition was observed macroscopically and microscopically on the posterior surface of the cornea of the eyeball recovered 2 days postsurgery (FIG. 7A left, middle). When the "eye with sphere and without viscoat" was microscopically observed, the sphere was enmeshed by fibrin and could not adhere to the cornea (FIG. 7B).

On the other hand, when a sphere was transplanted by the above-mentioned procedure and using the pharmaceutical composition for transplantation, fibrin deposition on the posterior surface of the cornea was not observed (FIG. 7A, right). The eyeball cornea was microscopically observed to find that sphere adhered to the posterior surface of cornea and spread and a therapeutic alternative corneal endothelial cell layer maintaining tight junction could be formed in 2 days postsurgery (FIG. 7C). ZO-1 and the nucleus were stained according to Example 1.

Figure 8:
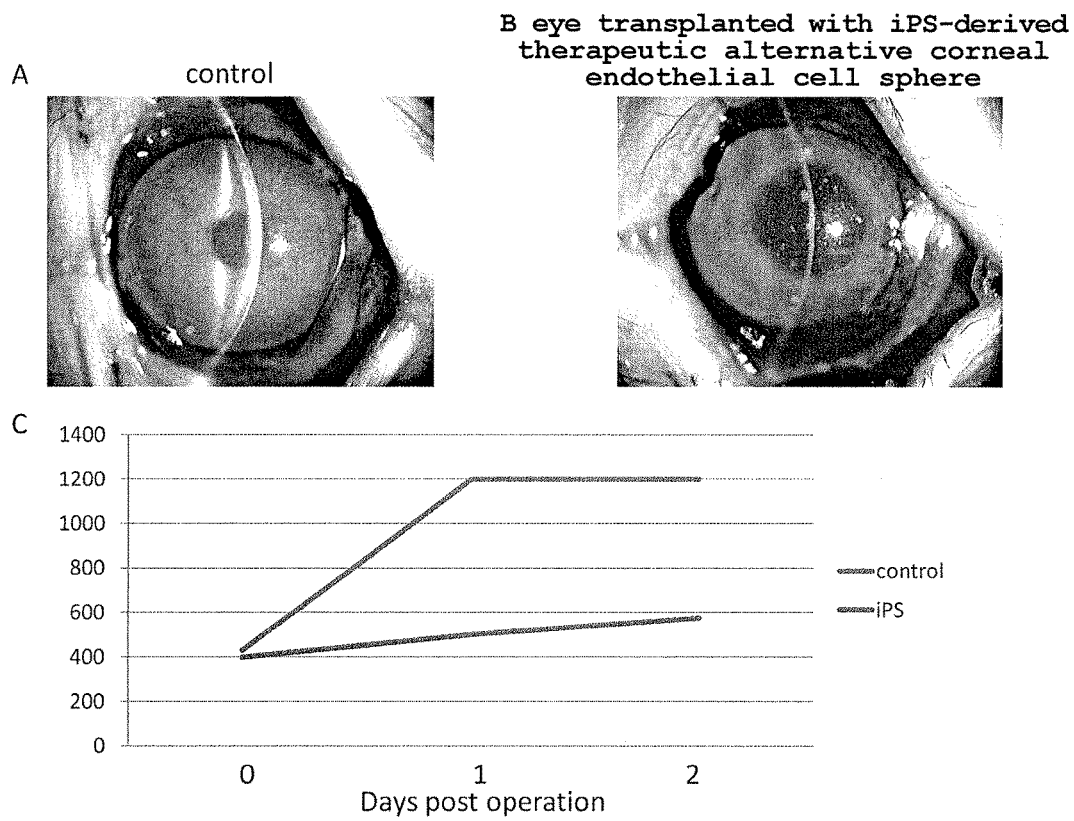
FIG. 8 shows examination results of corneal edema after transplanting the sphere of the present invention to the eye of *Macaca fascicularis*. In a control, corneal endothelial cells were detached without injecting the sphere (A). In the transplanted eye, the sphere was injected after detaching the corneal endothelium (B). In the transplanted eye, it was found that corneal edema was suppressed, and the corneal thickness could be maintained (C).

Furthermore, the sphere of the present invention was transplanted into the anterior chamber of *Macaca fascicularis*, from which the corneal endothelial cells had been detached, and the corneal thickness of the transplantation eye was measured immediately after transplantation, and one day and two days post-transplantation. The results are shown in FIG. 8. It is clear that the corneal edema was suppressed, and the corneal thickness could be maintained in the transplantation eye. In addition, an increase in the intraocular pressure was not observed, either.

Example 3

Cultured Corneal Endothelial Cell Transplantation Experiment

1. Pharmaceutical Composition for Transplantation, which to Contains Cultured Corneal Endothelial Cell Established cells of cultured corneal endothelial cell (B4G12 cells) were treated with an enzyme to give single cells.

A single cell suspension added with sodium hyaluronate (15 mg/ml) and chondroitin sulfate ester sodium (20 mg/ml) (suspension 1) and a single cell suspension not added with these but added with PBS instead (suspension 2) were prepared. As the additives other than sodium hyaluronate and chondroitin sulfate ester sodium, those similar to the additives described in Example 2, Table 1, were used at similar concentrations. The final cell density of suspensions 1 and 2 was adjusted to $1.0 \times 10^5$ cells/100 μl.
2. Transplantation of Cultured Corneal Endothelial Cells
(Procedure)

Using the pharmaceutical composition for transplantation prepared in the above-mentioned 1., cultured therapeutic alternative corneal endothelial cells were transplanted into the ocular anterior chamber by the following procedure.

(1) While refluxing the anterior chamber of rabbit (4) with saline, the endothelial side was rubbed to make the corneal endothelial cells fall off from a 8 mm diameter area.

(2) The anterior chamber after cell falling off was washed with saline.

(3) After washing, the pharmaceutical composition for transplantation prepared in the above-mentioned 1. was injected into the anterior chamber at 200 μl (=2.0×10$^5$ cells) per rabbit by using a 26 gauge syringe. Two rabbits each of a group injected with a pharmaceutical composition prepared using single cell suspension 1 (viscoelastic substance addition group), and a group injected with a pharmaceutical composition prepared using single cell suspension 2 (PBS addition group) were produced.

(4) The position of the rabbit was restricted for 3 hr to make the cells deposited and adhered onto the posterior surface of the cornea.

(5) After observation for 2 days, the eyeball was recovered and the range and density of adherent cells on the posterior surface of the cornea were evaluated.

(Results)

In the rabbits of the viscoelastic substance addition group, adhesion of the cells was confirmed over the whole 8 mm diameter area from which corneal endothelial cells were detached. On the other hand, in the rabbits of the PBS addition group, the adhesion area was as small as about 5 mm×6 mm as compared to the viscoelastic substance addition group.

Figure 9:
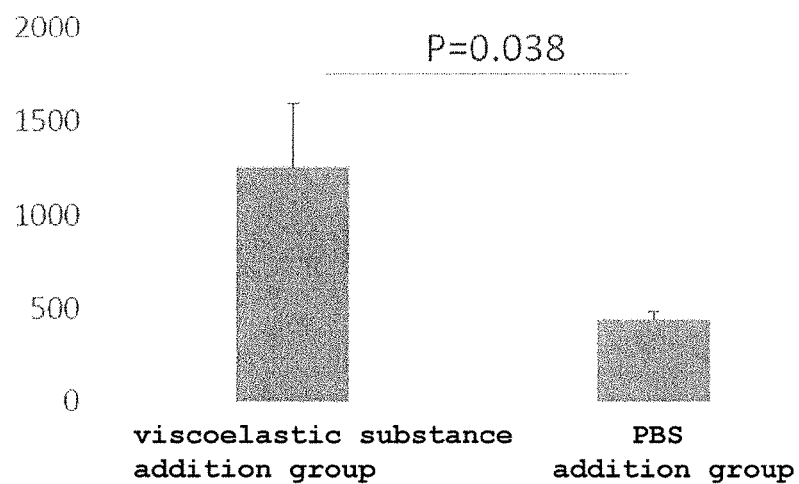
FIG. 9 is a graph showing evaluation of the density of the adhered cells in the posterior surface of cornea of the transplanted eye on day 2 after injecting (transplanting) cultured corneal endothelial cells into the anterior chamber of a rabbit by using (or without using) the pharmaceutical composition for transplantation of the present invention containing the cultured corneal endothelial cells and a viscoelastic substance. It was confirmed that the adhered cells increased after transplantation by adding the viscoelastic substance.

In each rabbit, any 4 points were selected in the area of detached corneal endothelial cells, the number of adherent cells at each point was counted under a microscope and the density thereof was calculated. The results are shown in the following Table 2 and FIG. 9.

It was clarified from these results that the adhesion density of the cells to the posterior surface of the cornea becomes significantly high by the addition of a viscoelastic substance in the method wherein a single cell suspension of cultured corneal endothelial cell was injected into the anterior chamber.

TABLE 2

|  | cell density (cells/mm$^2$) | |
| --- | --- | --- |
|  | viscoelastic substance | PBS |
| first rabbit | 1000 | 900 |
|  | 900 | 400 |
|  | 1000 | 200 |
|  | 1200 | 400 |
| second rabbit | 1700 | 400 |
|  | 1600 | 200 |
|  | 1500 | 200 |
|  | 1200 | 900 |

INDUSTRIAL APPLICABILITY

The present invention can produce a cell sphere, which is a precursor state of a therapeutic alternative corneal endothelial cell layer, from iPS cell, skin stem cell, and various other somatic stem cells by suspension culture. Since the sphere maintains intercellular tight junction, when the sphere is directly transplanted by injecting into the anterior chamber, it is adhered and spreads therefrom to rapidly achieve construction of a tissue of a therapeutic alternative corneal endothelial cell layer maintaining tight junction, as well as prevent EMT caused by stimulation such as dispersion of cells into single cells and the like.

Therefore, the present invention provides a method of efficiently transplanting induced therapeutic alternative corneal endothelial cells into the posterior surface of the cornea. This method enables clinical application of therapeutic alternative corneal endothelial cells induced from iPS cell, skin stem cell, and various other somatic stem cells.

This application is based on a patent application No. 2014-251236 filed in Japan (filing date: Dec. 11, 2014), the contents of which are incorporated in full herein.

The invention claimed is:

1. A pharmaceutical composition for transplantation comprising a therapeutic corneal endothelial cell sphere suspension having a cell density of 1-5×10$^6$ cells/ml, and a viscoelastic substance, wherein the viscoelastic substance is 5-40 mg/ml hyaluronic acid and/or 5-50 mg/ml chondroitin sulfate, and wherein the ratio of viscoelastic substance:cell sphere suspension is 1:1 to 1:5.

2. A pharmaceutical composition for transplantation comprising a cultured corneal endothelial cell suspension having a cell density of 1-5 ×10$^6$ cells/ml, and a viscoelastic substance, wherein the cultured corneal endothelial cells are dispersed as single cells or in the form of a cell aggregate, wherein the viscoelastic substance is 5-40 mg/ml hyaluronic acid and/or 5-50 mg/ml chondroitin sulfate, and wherein the ratio of viscoelastic substance:cell suspension is 1:1 to 1:5.

3. The pharmaceutical composition according to claim 1, which is for transplantation into anterior chamber.

4. The pharmaceutical composition according to claim 1, wherein the sphere of therapeutic corneal endothelial cells is obtained by a production method comprising culturing stem cells in suspension in a differentiation induction medium, wherein the differentiation induction medium comprises a GSK3inhibitor, retinoic acid and a ROCK inhibitor.

5. The pharmaceutical composition according to claim 2, wherein the cultured corneal endothelial cells in the suspension are dispersed into single cells.

6. The pharmaceutical composition according to claim 1, further comprising retinoic acid and a ROCK inhibitor.

7. The pharmaceutical composition according to claim 6, further comprising insulin, EGF and bFGF.

8. The pharmaceutical composition according to claim 2, which is for transplantation into anterior chamber.

9. The pharmaceutical composition according to claim 2, further comprising retinoic acid and a ROCK inhibitor.

10. The pharmaceutical composition according to claim 9, further comprising insulin, EGF and bFGF.

11. A method for improving cell engraftment during transplantation, comprising transplanting a corneal endothelial cell composition comprising (a) a cultured corneal endothelial cell suspension having a cell density of 1-5×10$^6$ cells/ml and (b) a viscoelastic substance into an anterior chamber of an eye, wherein the viscoelastic substance is 5-40 mg/ml hyaluronic acid and/or 5-50 mg/ml chondroitin sulfate, wherein the cells are dispersed into single cells or used in the form of a cell aggregate, wherein the ratio of viscoelastic substance:cell suspension is 1:1 to 1:5.

* * * * *